US008269025B2

(12) United States Patent
Belcheva et al.

(10) Patent No.: US 8,269,025 B2
(45) Date of Patent: Sep. 18, 2012

(54) PURIFICATION OF P-DIOXANONE

(75) Inventors: Nadya Belcheva, Hamden, CT (US);
Trang Huynh, Branford, CT (US);
Darlene Nebinger, Oxford, CT (US);
Ronald Rutka, Colchester, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 417 days.

(21) Appl. No.: 12/481,287

(22) Filed: Jun. 9, 2009

(65) Prior Publication Data
US 2010/0004471 A1    Jan. 7, 2010

Related U.S. Application Data

(60) Provisional application No. 61/077,934, filed on Jul. 3, 2008.

(51) Int. Cl.
*C07D 319/12*    (2006.01)
(52) U.S. Cl. .......................................... 549/378; 549/377
(58) Field of Classification Search ................. 549/377, 549/378
See application file for complete search history.

(56) References Cited

U.S. PATENT DOCUMENTS

| 7,232,863 | B2 | 6/2007 | Ohrbom et al. |
| 7,342,075 | B2 | 3/2008 | Ramesh et al. |

FOREIGN PATENT DOCUMENTS

| KR | 1999-0009205 | * | 2/1999 |

OTHER PUBLICATIONS

European Search Report for EP 09251705.1-2101 data of completion is Oct. 2, 2009 (3 pages).
XP002548513 Chemical Abstracts Service, Columbus, Ohio, US; Oct. 18, 2004 Database Accession No. 2008:912359 (abstract) JP 2008 174517 A (Mitsui Chemicals Inc.) Jul. 31, 2008.
XP002548514 Chemical Abstracts Service, Columbus, Ohio, US: Oct. 18, 2004 Database Accession No. 2004:853424 (abstract) KR 196 097 B (Samyang Corporation) Jun. 15, 1999.

\* cited by examiner

*Primary Examiner* — Taylor Victor Oh

(57) ABSTRACT

The present disclosure provides methods for purifying p-dioxanone. In embodiments, crude p-dioxanone may be contacted with at least one isocyanate-functionalized scavenger. The at least one isocyanate-functionalized scavenger may react with hydroxyl compounds present with the crude p-dioxanone to form reaction products, in embodiments polyurethanes and/or polyureas, which may then be removed. The p-dioxanone thus obtained is of greater purity than the starting crude p-dioxanone.

17 Claims, No Drawings

PURIFICATION OF P-DIOXANONE

CROSS-REFERENCE TO RELATED APPLICATIONS

This application claims the benefit of and priority to U.S. Provisional Application Ser. No. 61/077,934, filed Jul. 3, 2008, the entire disclosure of which is incorporated by reference herein.

TECHNICAL FIELD

The present disclosure relates to methods for purifying p-dioxanone. More particularly, the present disclosure relates to the purification of p-dioxanone using isocyanate-functionalized scavengers.

BACKGROUND OF RELATED ART

P-dioxanone (also known as 1,4-dioxan-2-one, para-dioxanone, and/or PDO) is a cyclic ester that undergoes ring-opening polymerization/copolymerization to form aliphatic polyesters. Besides outstanding biodegradability, bioabsorbability, and biocompatibility, poly(p-dioxanone) has unique physical properties, including its flexibility. Polymers made from p-dioxanone have been employed in the manufacture of absorbable medical/surgical devices. For example, p-dioxanone polymers and copolymers have received approval from the U.S. Food and Drug Administration (FDA) for, among other things, use as suture materials.

Various methods for the production of p-dioxanone are within the purview of those skilled in the art and include, for example, those disclosed in U.S. Pat. Nos. 4,052,988 and 5,391,707. Polymers made at least in part from p-dioxanone are also within the purview of those skilled in the art and include, for example, those disclosed in U.S. Pat. Nos. 4,643,191; 4,646,741; 4,653,497; 4,788,979; 4,838,267; 5,047,048; 5,007,923; 5,076,807; and 5,080,665. Other patents relating to the preparation of p-dioxanone include U.S. Pat. Nos. 3,020,289; 3,063,967; 3,190,858; 3,391,126; and 3,645,941. Methods for purifying p-dioxanone include those disclosed in U.S. Pat. Nos. 3,020,289; 3,063,967; and 5,391,768.

Improved methods for both producing and obtaining purified p-dioxanone remain desirable.

SUMMARY

The present disclosure provides methods for purifying p-dioxanone. In embodiments, a method of the present disclosure includes providing a starting material including crude p-dioxanone, contacting the starting material with an isocyanate-functional scavenger, allowing the isocyanate-functional scavenger to react with hydroxyl compounds in the starting material to form reaction products, removing the reaction products from the starting material, and recovering purified p-dioxanone compared to the crude p-dioxanone.

In other embodiments, methods of the present disclosure include providing a starting material including crude p-dioxanone, contacting the starting material with a solid isocyanate-functional scavenger such as 4-biphenyl isocyanate, 1,4-phenylene diisocyanate, 4,4'-methylene bis(phenyl isocyanate), and combinations thereof, allowing the isocyanate-functional scavenger to react with hydroxyl compounds in the starting material to form reaction products, removing the reaction products from the starting material, and recovering purified p-dioxanone having a purity of from about 40 mol % to about 99 mol %.

DETAILED DESCRIPTION

The methods of the present disclosure can be used to purify p-dioxanone which has been prepared by any method. For example, p-dioxanone can be prepared by the methods disclosed in U.S. Pat. Nos. 2,142,033; 2,900,395; 3,119,840; 4,070,375; 4,166,821; and 5,391,707, the entire disclosures of each of which are incorporated by reference herein.

In embodiments, a process for preparing p-dioxanone may include forming p-dioxanone from the dehydrogenation of diethylene glycol (DEG). The dehydrogenation of DEG may be carried out in the presence of a metallic catalyst. Such a catalyst can be a pure metal, e.g., copper, chromium, cobalt, iron, platinum, nickel, palladium, combinations thereof, and the like, or a mixture containing two or more metals, e.g., a copper-chromium mixture. In some embodiments, a copper-chromium catalyst may be utilized.

The temperature at which the dehydrogenation of DEG may be carried out can vary from about 200° C. to about 240° C., in embodiments from about 230° C. to about 235° C.

In embodiments, the resulting crude reaction-product including p-dioxanone may be dried with sodium bicarbonate or any other suitable drying agent and filtered to remove any impurities. The crude reaction product can be distilled under heat and reduced pressure to provide p-dioxanone in a greater yield than would otherwise be obtained.

In some embodiments, the formation of p-dioxanone from the dehydrogenation of DEG may occur while protecting the reactive hydrogens on DEG with unreactive groups as disclosed in U.S. Pat. No. 5,391,707. Protecting the reactive hydrogens on DEG with unreactive groups, sometimes referred to as "blocking," will prevent polymerization of p-dioxanone prior to recovery.

Regardless of how prepared, the product which is to be purified by the methods of the present disclosure may be referred to herein, in embodiments, as a "crude reaction product", "crude starting material," or "crude p-dioxanone," with these terms being used interchangeably. The terms "crude reaction product", "crude starting material," and/or "crude p-dioxanone" are also intended to embrace any mixture or combination of materials produced during the production of p-dioxanone. Thus, crude p-dioxanone may contain not only p-dioxanone, but may also contain unreacted starting materials and other compounds employed in forming p-dioxanone, including hydroxyl compounds such as water, aliphatic hydroxyl compounds such as ethylene glycol, diethylene glycol, triethylene glycol, linear oligomers of p-dioxanone, combinations thereof, and the like.

It should also be understood that the crude p-dioxanone may be subject to one or more processes such as, for example, distillation, washing and/or filtration prior to purification by the methods of the present disclosure. Thus, the terms "crude reaction product", "crude starting material," and/or "crude p-dioxanone" are also intended to embrace a reaction product which has been subjected to such processes. The crude p-dioxanone may have a purity of from about 30 mol % to about 90 mol %, in embodiments from about 50 mol % to about 80 mol %.

In embodiments, the p-dioxanone may be in a solution. Any solvent within the purview of those skilled in the art may be utilized to form such a solution. Such solvents include, for example, tetrahydrofuran, dioxane, dimethylformamide (DMF), dimethylsulfoxide (DMSO), combinations thereof, and the like. The crude p-dioxanone may be dissolved in the solvent to form a solution. The amount of crude p-dioxanone dissolved in the solvent may be from about 50 grams per liter of solution to about 1000 grams per liter of solution, in embodiments from about 100 grams per liter of solution to about 600 grams per liter of solution, depending on a number of factors including the reaction used to prepare the p-dioxanone, the reaction conditions employed, and the composition of the resulting crude reaction product. Where diethylene glycol is used to prepare the p-dioxanone, the amount of dissolved crude p-dioxanone may be from about 600 grams per liter of solution to about 1000 grams per liter of solution.

Once obtained, the crude p-dioxanone may be purified with an isocyanate-functionalized scavenger. In embodiments, the isocyanate-functionalized scavenger may be in a solid form. Suitable isocyanate-functionalized scavengers include diisocyanates, polyisocyanates, aromatic isocyanates, polymer-supported isocyanates, cross-linked isocyanates, combinations thereof, and the like. Specific examples of isocyanate-functionalized scavengers include, but are not limited to, 4-biphenyl isocyanate, 1,4-phenylene diisocyanate, 4,4'-methylenebis(phenyl isocyanate) (4,4-MDI), combinations thereof, and the like.

In other embodiments, the isocyanate-functionalized scavenger may be in a solution, suspension, dispersion, or emulsion formed by combining the isocyanate-functionalized scavenger with a suitable solvent. Such solvents include, but are not limited to, tetrahydrofuran, dioxane, dimethylformamide (DMF), dimethylsulfoxide (DMSO), combinations thereof, and the like.

The amount of isocyanate-functionalized scavenger added to the crude p-dioxanone may be from about 5% by weight of the crude p-dioxanone to about 50% by weight of the crude p-dioxanone, in embodiments from about 10% by weight of the crude p-dioxanone to about 20% by weight of the crude p-dioxanone.

The crude p-dioxanone and isocyanate-functionalized scavenger may be combined utilizing any method within the purview of those skilled in the art, including mixing, blending, shaking, sonication, stirring, combinations thereof, and the like, for a suitable period of time of from about 1 hour to about 24 hours, in embodiments from about 2 hours to about 24 hours, in other embodiments from about 2.25 hours to about 3.5 hours. Mixing may occur at a rate of from about 0 rpm to about 500 rpm, in embodiments from about 100 rpm to about 200 rpm. The crude p-dioxanone and isocyanate-functionalized scavenger may be combined at a suitable temperature, in embodiments at room temperature of from about 20° C. to about 25° C. In embodiments, combining may occur under an inert atmosphere, for example, an atmosphere of nitrogen, helium, argon, combinations thereof, and the like.

Without wishing to be bound by any theory, it is believed that the isocyanate-functionalized scavenger(s) react selectively with hydroxyl compounds in the crude reaction product, including water, as well as aliphatic hydroxyl compounds such as ethylene glycol, diethylene glycol, triethylene glycol, linear oligomers of p-dioxanone, combinations thereof, and the like, by forming polyurethanes and/or polyureas. The polyurethanes and/or polyureas thus formed may then be removed by methods within the purview of those skilled in the art, for example by decanting and/or filtering from the liquid phase, column purification, centrifugation, combinations thereof, and the like.

For example, the mixture including the p-dioxanone and polyurethanes and/or polyureas formed by the reaction of the isocyanate-functionalized scavenger with hydroxyl compounds in the crude p-dioxanone may be filtered from about 1 time to about 5 times, in embodiments from about 2 times to about 4 times. In embodiments, decanting and/or filtering may be repeated and/or modified by using column purification to optimize yields and purity of the final product. Column purification generally involves introducing the material to be purified through a column where the desired products flow through the column unrestrained, while other reaction constituents are retained in the column. For example, in some embodiments, a column can be constructed that may have constituents therein that will bind to the polyurethanes and/or polyureas formed by the reaction of the isocyanate-functionalized scavenger with hydroxyl compounds, thereby removing the formed polyurethanes and/or polyureas from the purified p-dioxanone. In other embodiments, columns may be constructed that have constituents therein that will bind impurities having hydroxy groups. Examples of such columns include, for example, solid isocyanates, polyisocyanates, polymer-supported isocyanate resins, combinations thereof, and the like. In some embodiments, the crude p-dioxanone may be contacted with the isocyanate-functionalized scavengers in a column, with the impurities containing hydroxy groups reacting with the isocyanate-functionalized scavengers described above in the column and becoming restrained in the column, so that the purified p-dioxanone may pass through the column unrestrained.

Utilizing the methods of the present disclosure, p-dioxanone may be prepared having a purity of from about 40 mol % to about 99 mol %, in embodiments from about 50 mol % to about 90 mol %. The p-dioxanone thus produced may have a purity of from about 40 mol % to about 100 mol % greater than the purity of the crude p-dioxanone, in embodiments from about 60 mol % to about 99 mol % greater than the purity of the crude p-dioxanone.

In other embodiments, additional and different purification steps may be utilized to further purify p-dioxanone obtained by the methods of the present disclosure. Additional methods for obtaining highly pure p-dioxanone from reaction products containing p-dioxanone include crystallization techniques, such as the processes disclosed in U.S. Pat. No. 5,391,768, the entire disclosure of which is incorporated by reference herein. The method disclosed therein includes the steps of forming a solution by dissolving crude p-dioxanone in an aliphatic ester, forming p-dioxanone crystals from the solution to provide a mixture and filtering the mixture to recover pure p-dioxanone. The steps can be repeated to obtain p-dioxanone of very high purity, e.g., purity on the order of 99% and higher.

Dioxanone obtained by the methods of the present disclosure can be polymerized by itself or combined with other copolymerizable monomers, e.g., glycolide, lactide, trimethylene carbonate, caprolactone, combinations thereof, and the like. The resulting homopolymers and/or copolymers can be linear, branched, or star shaped, and can be random, block or graft copolymers. In addition, the polymers may be blended with other bioabsorbable polymers. The characteristics of the resulting polymer or blend can be tailored to desired specifications by controlling the composition, reaction conditions and/or blending parameters.

The methods herein avoid the use of certain compounds, including halogenated compounds, thereby minimizing the environmental impact and any adverse health issues that may arise from the use of such compounds. The purification of the crude p-dioxanone with the isocyanate-functionalized scavengers described herein is also simple and economical, as it avoids the need for time-consuming multiple distillations and re-crystallizations that may be necessary utilizing other methods to purify the p-dioxanone.

Bioabsorbable polymers utilized to produce surgical devices should possess a high degree of purity, as the polymers decompose and become absorbed within the body. The high yield and purity of the p-dioxanone obtained in accordance with the present disclosure may be beneficial in the synthesis of polymers and co-polymers that, in turn, may be utilized in the formation of medical devices. The polymers and/or copolymers can be used in the fabrication of a wide variety of medical/surgical devices, e.g., sutures, screws, staples, tacks, clips, pins, prostheses, buttresses, pledgets, mesh, scaffolds, drug delivery systems, composite constructs, orthopedic devices such as bone anchors and interference screws, and the like. Methods for producing such devices are within the purview of those skilled in the art. For example, the polymers and/or compounds formed with dioxanone monomers prepared in accordance with the present disclosure can be formed into useful articles by methods including molding, casting, pressing, grinding, extruding, spinning, electro-spinning, combinations thereof, and the like.

The following Examples are provided as an illustration of embodiments of the present disclosure. The Examples are intended to be illustrative only and are not intended to limit the scope of the present disclosure. Also, parts and percentages are by weight unless otherwise indicated. As used here, "room temperature" refers to a temperature of from about 20° C. to about 25° C.

EXAMPLE

About 36.8 grams of crude p-dioxanone was produced following the procedures set forth in U.S. Pat. No. 5,391,768, having a purity of about 57.6 mol % (thus having about 0.144 moles, or 42.4%, of diethylene glycol). Briefly, about 130 grams of diethylene glycol (DEG) and about 2 grams of copper chromite were refluxed for about 6 hours. The reaction mixture was distilled and a crude p-dioxanone with a purity of about 57.6 mol % (42.4 mol % DEG) was collected. About 3.7 grams (about 10% by weight) of 1,4-phenylene diisocyanate from Sigma Aldrich was combined with about 36.8 grams of crude p-dioxanone in a 100 mL flask and stirred for about 3 hours at about 22° C. under a nitrogen blanket. The reaction was monitored in situ by Fourier Transform Infrared Spectroscopy (FT-IR) using a REACTIR™ 4000 Spectrometer (Mettler-Toledo AutoChem, Columbia, Md.), as well as proton nuclear magnetic resonance spectroscopy ($^1$H-NMR) run at about 300 MHz; the ReactIR probe was inserted into the flask; the background utilized was air.

The IR results showed a peak indicative of free NCO groups, at 2266 cm$^{-1}$, which decreased during the course of the reaction. After about 1.5 hours, there was no peak from NCO groups due to their reaction with the hydroxyl compounds. The $^1$H-NMR spectra of the starting crude p-dioxanone showed about 57.6 mol % purity; after about 3 hours of reacting with 1,4-phenylene diisocyanate, the purity was increased to about 61.9 mol %. The reaction mixture was left for about 72 hours without stirring. The $^1$H-NMR spectra obtained after about 72 hours showed no change in the molar percentage of the p-dioxanone in the reaction mixture.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method comprising:
    providing a starting material comprising crude p-dioxanone;
    contacting the starting material with an isocyanate-functional scavenger;
    conducting a catalyst-free reaction of the isocyanate-functional scavenger with hydroxyl compounds in the starting material at a temperature of from about 20° C. to about 25° C. to form reaction products;
    removing the reaction products from the starting material by a method selected from the group consisting of decanting, filtration, column purification, centrifugation, and combinations thereof; and
    recovering purified p-dioxanone.

2. The method of claim 1, wherein the crude p-dioxanone in the starting material has a purity of from about 30 mol % to about 90 mol %.

3. The method of claim 1, wherein the crude p-dioxanone in the starting material has a purity of from about 50 mol % to about 80 mol %.

4. The method of claim 1, wherein the isocyanate-functional scavenger is selected from the group consisting of diisocyanates, polyisocyanates, aromatic isocyanates, polymer-supported isocyanates, and combinations thereof.

5. The method of claim 1, wherein the isocyanate-functional scavenger is selected from the group consisting of 4-biphenyl isocyanate, 1,4-phenylene diisocyanate, 4,4'-methylenebis(phenyl isocyanate) (4,4-MDI), and combinations thereof.

6. The method of claim 1, wherein allowing the isocyanate-functional scavenger to react with hydroxyl compounds in the starting material occurs over a period of time of from about 1 hour to about 24 hours.

7. The method of claim 1, wherein allowing the isocyanate-functional scavenger to react with hydroxyl compounds in the starting material occurs while mixing at a rate of from about 0 rpm to about 500 rpm.

8. The method of claim 1, wherein allowing the isocyanate-functional scavenger to react with hydroxyl compounds in the starting material occurs under an inert atmosphere selected from the group consisting of nitrogen, helium, argon, and combinations thereof.

9. The method of claim 1, wherein the purified p-dioxanone has a purity of from about 40 mol % to about 99 mol %.

10. The method of claim 1, wherein the purified p-dioxanone has a purity of at least greater than about 50 mol %.

11. A method comprising:
    providing a starting material comprising crude p-dioxanone;
    contacting the starting material with a solid isocyanate-functional scavenger selected from the group consisting of 4-biphenyl isocyanate, 1,4-phenylene diisocyanate, 4,4'-methylene bis(phenyl isocyanate), and combinations thereof;
    conducting a catalyst-free reaction of the isocyanate-functional scavenger with hydroxyl compounds in the starting material at a temperature of from about 20° C. to about 25° C. to form reaction products;
    removing the reaction products from the starting material by a method selected from the group consisting of decanting, filtration, column purification, centrifugation, and combinations thereof; and
    recovering purified p-dioxanone having a purity of from about 40 mol % to about 99 mol %.

12. The method of claim 11, wherein the crude p-dioxanone has a purity of from about 30 mol % to about 90 mol %.

13. The method of claim 11, wherein the crude p-dioxanone has a purity of from about 50 mol % to about 80 mol %.

14. The method of claim 11, wherein allowing the isocyanate-functional scavenger to react with hydroxyl compounds in the starting material occurs over a period of time of from about 2 hours to about 10 hours.

15. The method of claim 11, wherein allowing the isocyanate-functional scavenger to react with hydroxyl compounds in the starting material occurs while mixing at a rate of from about 100 rpm to about 200 rpm.

16. The method of claim 11, wherein allowing the isocyanate-functional scavenger to react with hydroxyl compounds in the starting material occurs under an inert atmosphere selected from the group consisting of nitrogen, helium, argon, and combinations thereof.

17. The method of claim 11, wherein the purified p-dioxanone has a purity of from about 50 mol % to about 90 mol %.

* * * * *